(12) United States Patent
Vincent

(10) Patent No.: US 7,944,219 B2
(45) Date of Patent: May 17, 2011

(54) AMPEROMETRIC ELECTROCHEMICAL SENSOR

(75) Inventor: David Robert Vincent, Ferndown (GB)

(73) Assignee: Intellitect Water Limited, Dorset (GB)

( * ) Notice: Subject to any disclaimer, the term of this patent is extended or adjusted under 35 U.S.C. 154(b) by 330 days.

(21) Appl. No.: 12/087,851

(22) PCT Filed: Jan. 18, 2007

(86) PCT No.: PCT/GB2007/000161
§ 371 (c)(1),
(2), (4) Date: Jul. 16, 2008

(87) PCT Pub. No.: WO2007/083129
PCT Pub. Date: Jul. 26, 2007

(65) Prior Publication Data
US 2010/0148754 A1    Jun. 17, 2010

(51) Int. Cl.
*G01R 27/08* (2006.01)
*G01N 27/49* (2006.01)
(52) U.S. Cl. ....................................................... 324/693
(58) Field of Classification Search .................. None
See application file for complete search history.

(56) References Cited

U.S. PATENT DOCUMENTS

| 4,997,526 A | 3/1991 | Robblee | |
|---|---|---|---|
| 5,470,484 A | 11/1995 | McNeel | |
| 6,790,341 B1 * | 9/2004 | Saban et al. | 205/775 |
| 2003/0152960 A1 | 8/2003 | Thorp et al. | |
| 2009/0293590 A1 * | 12/2009 | Zeng et al. | 73/24.06 |

FOREIGN PATENT DOCUMENTS

| EP | 0833149 A | 4/1998 |
|---|---|---|
| EP | 833149 A1 * | 4/1998 |

* cited by examiner

*Primary Examiner* — Paresh Patel
(74) *Attorney, Agent, or Firm* — Iandiorio Teska & Coleman

(57) ABSTRACT

Apparatus (2) for driving an amperometric electrochemical sensor, which apparatus (2) comprises a microelectrode (30), drive means (36) for the microelectrode, and signal processing means (3), the apparatus (2) being such that the drive means (36) supplies successive pulsed chronoamperometric different conditions to the microelectrode (30), the microelectrode (30) produces a sequence of different voltages consequent upon receiving the chronoamperometric different conditions and correlates the received chronoamperometric different conditions with their respective measurement circuits, and the signal processing means (3) interrogates only the current corresponding to a particular voltage in the sequence of different voltages and thereby produces a single sensor output corresponding to each separate voltage in the sequence of different voltages whereby interrogation of the amperometric electrochemical sensor is facilitated.

6 Claims, 2 Drawing Sheets

AMPEROMETRIC ELECTROCHEMICAL SENSOR

FIELD OF THE INVENTION

This invention relates to an amperometric electrochemical sensor. The amperometric electrochemical sensor utilises signal processing which is such that it is possible to obtain more than one output from the amperometric electrochemical sensor. The outputs may be compatible with simple electronic interrogation circuits, giving a fast response time.

DESCRIPTION OF RELATED ART

The use of chronoamperometry in combination with microband electrochemical sensors is well known and is described in the Oldham equation. The known method uses a step change in electrobias potential to achieve a diffusion limited decaying signal that is largely independent of flow. A typical laboratory approach to making measurements with this method is to integrate the current output of the microband electrochemical sensor over a period of time, for example, one minute, to achieve a value for the total charge passed, which is a measurement of the concentration of the chemical under study. The method is not sufficiently robust to changes in chemical flow. Also, the method is not fast enough for taking measurements in real conditions outside a laboratory. Also, the method does not easily provide a steady voltage output that can be interrogated with simple electronics. Also, the method does not lend itself to measuring more than one parameter quickly and conveniently.

BRIEF SUMMARY OF THE INVENTION

It is an aim of the present invention to obviate or reduce at least some of the above mentioned problems.

Accordingly, the present invention provides an amperometric electrochemical sensor which comprises a microelectrode, drive means for the microelectrode, a current to voltage converter, measurement circuits for chronoamperometric different conditions, signal processing means, and sampling means, the amperometric electrochemical sensor being such that the drive means supplies successive pulsed chronoamperometric different conditions to the microelectrode, the microelectrode and the current to voltage converter produce a sequence of different voltages consequent upon receiving the chronamperometric different conditions and correlate the received chronoamperometric different conditions with their respective measurement circuits, and the signal processing means interrogates only the microelectrode output signal corresponding to a particular voltage in the sequence of different voltages and thereby produces a single sensor output corresponding to each separate voltage in the sequence of different voltages whereby interrogation of the amperometric electrochemical sensor is facilitated, and the microelectrode output corresponding to a particular voltage in the sequence of different voltages is only interrogated in the early part of the microelectrode output signal when the microelectrode output signal is at its highest and before it reaches a steady state.

With the present invention, the interrogation of the amperometric electrochemical sensor is able to be quick and easy. The present invention enables a single amperometric electrochemical sensor to be used to measure a number of different chemicals. Also, the present invention is able to improve the accuracy of each of the measurements obtained, and does not require the use of a membrane or measurement chemicals.

The current flows through the microelectrode depend upon the sequence of different voltages produced by the microelectrode, and they are generally proportional to the concentration of the chemical of interest in the water or other liquid. Because concentration of the chemical of interest decays as the electrochemical sensor current flows, the voltage reaches an appropriate value and the current becomes flow sensitive. In order to eliminate this flow sensitivity, current measurements need to take place a few milliseconds after the voltage changes (5 mS-100 mS). The apparatus of the present invention enables the current to be sampled and integrated over several cycles to give an easy-to-measure steady voltage. In contrast, a prior art microprocessor would have to work hard to read the value directly, and would use substantial current, which is not used by the apparatus of the present invention. A true microelectrode would not have the current decay problem, but the problem is in any event able to be overcome because the microelectrode has dimensions small enough to make the signal to the electrode depend only on diffusion, and not on bulk flow. For a bigger electrode, the sampling time and capacitance required would make the apparatus unworkable.

Preferably, the microelectrode is a microband. If desired however the microelectrode may be a microdot or other shape with a fast electrochemical reaction time.

The microelectrode, for example the microband, may be made of gold or platinum. The microelectrode will usually be placed in water that is having its parameters measured. When the microelectrode is a microband, then the microband may be, for example, 3-5 mm long and 5-20 micron thick.

The sampling means is preferably a sample and hold circuit. The sample and hold circuit is able to generate a number of steady voltages instead of a single, quickly varying voltage which would need to be measured constantly be a microprocessor. The sample and hold circuit is therefore able to make operation of the amperometric electrochemical sensor autonomous from core microprocessor operations. With the present invention, it may only be necessary to measure the output voltage when required, for example every few minutes, and overall power consumption is thereby reduced.

The amperometric electrochemical sensor may include a pulse sequence generator for controlling sampling frequency and duration. This may be effected by the pulse sequence generator controlling the sampling frequency and duration of the sample and hold circuit, or circuits where more than one circuit is employed.

The amperometric electrochemical sensor may include a voltage sequence generator for generating a series of voltage steps, with each voltage corresponding to a different bias voltage for the microelectrode. Since each bias voltage may be used to detect a different chemical, the voltage sequence generator provides a means for programming selectivity into the device.

The amperometric electrochemical sensor may include transducer means for converting a pulsed electrochemical signal to a series of steady analogue voltages. The use of the transducer means is advantageous in that the series of steady analogue voltages are more convenient to measure than a pulsed electrochemical signal.

The amperometric electrochemical sensor may operate such that part of the voltage sequence is switching between a value where chemical-concentration-dependent electrochemical current does not flow, and a value where a current does flow. Directly after this change takes place, the current goes very high and then decays as the chemical reacts and its local concentration is depleted. The time after switching the voltage that the current is measured should normally be the same for each cycle in order to get stable readings. The signal processing converts the current into a voltage for measuring.

The amperometric electrochemical sensor is especially useful for measuring parameters in water supplies such for example as the content of chlorine, inorganic chloramines, and oxygen.

The amperometric electrochemical sensor may be used to sample current output a short time after the potential step (for example a time of the order of 100 mS, but which could be more or less, as limited by the strength of the signal and the capacitance of the sensor and electronics), and measure a current that is proportional to concentration. Since this measurement can be made quickly, it becomes possible to apply a series of different potential steps to the electrode, and measure a series of different current responses, each corresponding to a different electrochemical response, possibly to a different chemical. The output of the sensor is thus a series of time-multiplexed responses that, by correlation with the potential step, can be de-multiplexed and integrated into a set of voltage outputs, which change smoothly with changes in concentration of the measurand. These measurements can be used together to extract secondary dependencies and zero offsets from the sensor response to the primary measurand of interest. For example, a chlorine response can be subtracted from a dissolved oxygen plus chlorine response, in order to give a dissolved oxygen in potable water measurement that is independent of chlorine present. To achieve this using known conventional measurement techniques would require either more sensors or much more time. Another example of the use of the present invention is in the measurement of chloramines in water, in which case the chlorine response is able to be subtracted.

BRIEF DESCRIPTION OF THE DRAWINGS

An embodiment of the invention will now be described solely by way of example and with reference to the accompanying drawings in which.

DETAILED DESCRIPTION OF THE DRAWINGS

Figure 1:
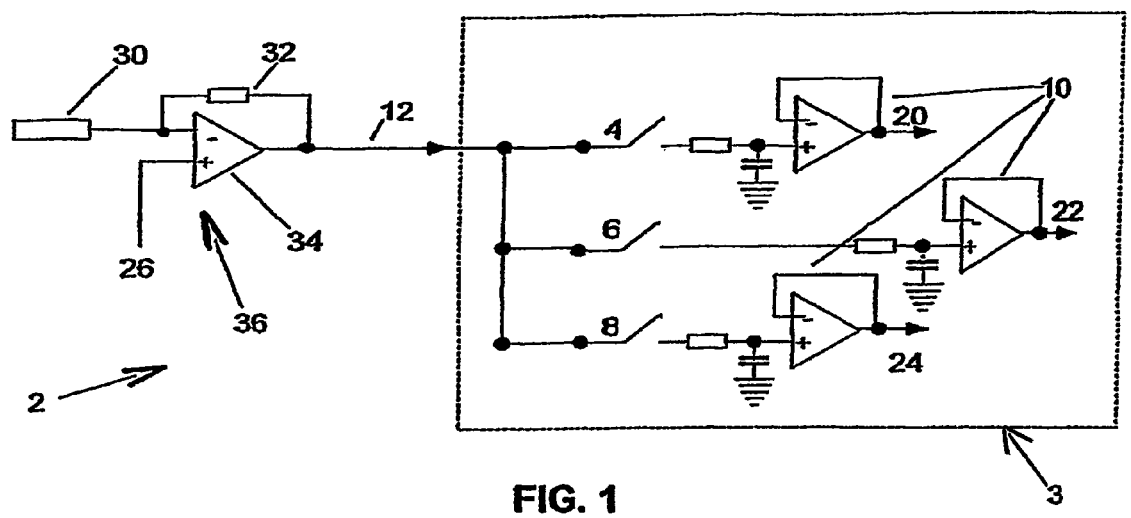
FIG. 1 shows an amperometric electrochemical sensor.

Referring to FIG. 1, there is shown an amperometric electrochemical sensor 2. More specifically, the amperometric electrochemical sensor 2 comprises signal processing means 3 and three switches 4, 6, 8. The signal processing means 3 may be regarded as voltage processing means. Each switch 4, 6, 8 is connected to its own sample and hold circuit 10 as shown. The amperometric electrochemical sensor 2 is shown with the signal processing means 3 receiving a sensor signal input 12. This sensor signal input 12 is connected to the three switches 4, 6, 8. The switches 4, 6, 8 are switched by signals 14, 16, 18 shown in FIG. 2. The sensor signal input 12 is then able to pass to the sample and hold circuits 10. The sample and hold circuits 10 then generate steady state signals 20, 22, 24 as shown.

Figure 2:
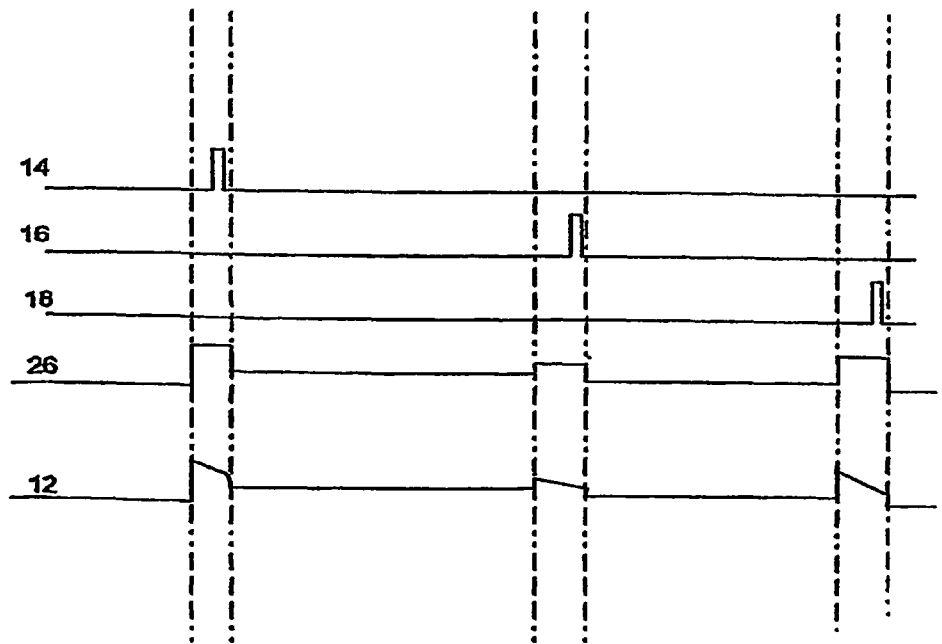
FIG. 2 is a diagram of signals going to sensor circuit and the sensor output as a result.

FIG. 2 shows the sensor signal input 12, the signals 14, 16, 18, and a sensor bias voltage signal 26. The sensor bias voltage signal 26 is shown in FIGS. 1 and 2, and it is cycled between values selected to match the electrochemical potentials of the chemicals being measured. The sample and hold circuits 10 shown in FIG. 1 are used to measure the signal sensor input 12 at specific times in the bias voltage cycle, as indicated by the signals 14, 16, 18. Thus the rapidly changing sensor signal input 12 is converted into a slowly changing integrated voltage that can be measured as required. By way of example it is mentioned that signal pulses may be 10-200 mS long, and spaced 0.5-5 seconds apart.

FIG. 1 also shows a microelectrode in the form of a microline electrode 30. In use, the microline electrode 30 is fully immersed in a measurand liquid. The measurand liquid will usually be water but it may be another liquid if desired.

Also shown in FIG. 1 is a current-to-voltage converter resistor 32, and an input operational amplifier 34 which forms part of drive means in the form of a microline drive circuit 36. The microline drive circuit 36 has a first input in the form of a microline electrode 30, a second input in the form of the sensor bias voltage 26, and an output in the form of the signal sensor input 12 for the sample and hold circuits 10.

Figure 3:
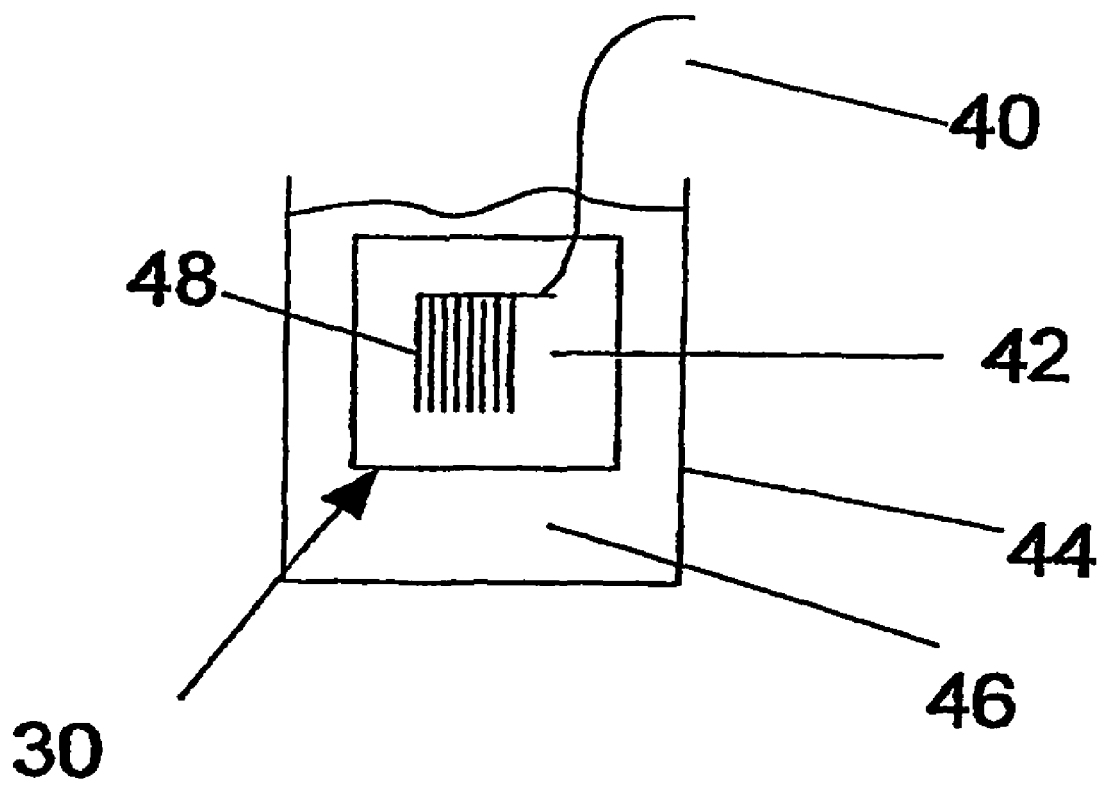
FIG. 3 shows how the amperometric electrochemical sensor shown in FIG. 1 may be used.

FIG. 3 shows the microline electrode 30 having a microline 48 on a substrate 42. The microline 48 is connected by a wire to a circuit 40. The microline electrode 30 is exposed to a measurand liquid 46 held in a container 44. The container 44 may be, for example, a pipe, a closed container, or a flowcell.

It is to be appreciated that the embodiment of the invention described above with reference to the accompanying drawings has been given by way of example only and that modifications may be effected. Thus, for example, in FIG. 3 the microline 48 may be implemented in a different way, and the container 44 may be other than a pipe, a closed container, or a flowcell.

The invention claimed is:

1. An amperometric electrochemical sensor which comprises a microelectrode, drive means for the microelectrode, a current to voltage converter, measurement circuits for chronoamperometric different conditions, signal processing means, and sampling means, the amperometric electrochemical sensor being such that the drive means supplies successive pulsed chronoamperometric different conditions to the microelectrode, the microelectrode and the current to voltage converter produce a sequence of different voltages consequent upon receiving the chronamperometric different conditions and correlate the received chronoamperometric different conditions with their respective measurement circuits, and the signal processing means interrogates only the microelectrode output signal corresponding to a particular voltage in the sequence of different voltages and thereby produces a single sensor output corresponding to each separate voltage in the sequence of different voltages whereby interrogation of the amperometric electrochemical sensor is facilitated, and the microelectrode output corresponding to a particular voltage in the sequence of different voltages is only interrogated in the early part of the microelectrode output signal when the microelectrode output signal is at its highest and before it reaches a steady state.

2. An amperometric electrochemical sensor according to claim 1 in which the microelectrode is a microband.

3. An amperometric electrochemical sensor according to claim 1 in which the sampling means is a sample and hold circuit.

4. An amperometric electrochemical sensor according to claim 1 and including a pulse sequence generator for controlling sampling frequency and duration.

5. An amperometric electrochemical sensor according to claim 1 and including a voltage sequence generator for generating a series of voltage steps, with each voltage corresponding to a different bias voltage for the microelectrode.

6. An amperometric electrochemical sensor according to claim 1 and including transducer means for converting a pulsed electrochemical signal to a series of steady analogue voltages.

* * * * *